United States Patent
Coop et al.

(10) Patent No.: US 6,291,675 B1
(45) Date of Patent: Sep. 18, 2001

(54) METHODS OF O-DEMETHYLATION AND N-DEPROTECTION

(75) Inventors: Andrew Coop, Baltimore; Kenner C. Rice, Bethesda, both of MD (US)

(73) Assignee: The United States as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/194,510

(22) PCT Filed: May 21, 1997

(86) PCT No.: PCT/US97/08628

§ 371 Date: Jul. 6, 1999

§ 102(e) Date: Jul. 6, 1999

(87) PCT Pub. No.: WO97/44317

PCT Pub. Date: Nov. 27, 1997

Related U.S. Application Data

(60) Provisional application No. 60/018,027, filed on May 21, 1996, and provisional application No. 60/020,215, filed on Jun. 21, 1996.

(51) Int. Cl.[7] .................. C07D 489/02; C07D 491/22
(52) U.S. Cl. ................... 546/44; 546/35; 546/39
(58) Field of Search .................. 546/35, 39, 44

(56) References Cited

FOREIGN PATENT DOCUMENTS

| 0 534 536 | 3/1993 | (EP) . |
| 97/44317 | 11/1997 | (WO) . |

OTHER PUBLICATIONS

Fleischhacker, W. et al.: 14–Alkyl substituted morphine–d-erivative. Chem. Ber. vol. 112, pp. 2539–2551, 1979.*

Barber et al., "Synthesis of Thebaine and Oripavine from Codeine and Morphine," *Journal of Medicinal Chemistry*, 18 11, 1074–1077 (1975).

Bentley et al., "Novel Analgesics and Molecular Rearrangements in the Morphine–Thebaine Group. III. Alcohols of the 6,14–endo–Ethenotetrahydrooripavine Series and Derived Analogs of N–Allylnormorphine and norcodeine," *Journal of the American Chemical Society*,89 13, 3281–3292.

Bentley, K.W., "The Morphine–Thebaine Group of Alkaloids. IX. The Reaction of Thebaine with Magnesium Iodide," *Journal of the American Chemical Society*,89 10 2464–2469 (1967).

Calderon et al., "Probes of Narcotic Receptor Mediated Phenomena. 19. Synthesis of (=)-4[(αR)-α-((2S, 5R)-4-Allyl-2,5-dimethyl-1-piperazinyl)-3-methoxybenzyl]-N,N-diethylbenzamide (SNC 80): A Highly Selective, Nonpeptide δ Opiod Receptor Antagonist," *Journal of Medicinal Chemistry*, 37, 2125–2128 (1994).

Casy, Alan F., "Opioid Analgesics," *Plenum Press*, 89, 54–55 and 71–73 (1986).

Fleischhacker et al., "14–Alkyl–Substituierte Morphine–Derivative," *Chem. Ber.*, 112, 2539–2551 (1979).

Lawson et al., "An Improved Method for O–Dimethylation of Codeine," *The Journal of Medicinal Chemistry*, 20 1, 165–166 (1977).

Link, J.T., "Regloselective Imide Reduction: An Issue in the Total Synthesis of Stauroaporine," *Tetrahedron Letters*, 35 9, 9135–9138 (1994).

Majetich et al., "Hydride–promoted Demethylation of Methyl Phenyl Ethers," *Tetrahedron Letters*,35 47, 8727–8730 (1994).

Marton et al., "Preparation of 6,14–Ethenomorphinan Derivatives," *Chemical Monthly*,125, 1229–1239 (1994) *Abstract included.

Mathis et al., "Synthesis and Preliminary In Vivo Evaluation of [$^{11}$C]MDL 100907: A Potent and Selective Radioligand for the 5–HT$_{2A}$ Receptor System," *Med. Chem. Res.*, 6, 1–10 (1996).

Monovic et al., Oxilporphan and Butorphanol. Potent Narcotic Antagonists and Nonaddicting Analgesics in the 3,14–Dihydroxymorphinan Series. Part V. *Canadian Journal of Chemistry*, 53, 3094–3102.

Rappaport et al., "The Synthesis of Thebaine and Northebaine," *Journal of the American Chemical Society*,89 8, 1942–1947 (1967).

Rice, Kenner C., "A Rapid, High Yield Conversion of Codeine to Morphine," *Journal of Medicinal Chemistry*, 20 1, 164–165 (1977).

Rice, Kenner C., "An Improved Procedure for the N–Demethylation of 6,7 Benzomorphans, Morphine and Codeine," *Journal of Organic Chemistry*, 40 12, 1850–1851 (1975).

Schmid et al., "Uber das β–Dihydro–thebain," *Helvetica Chimica Acta.*, 115, 863–873 (1950) *No Translation.

* cited by examiner

*Primary Examiner*—Charanjit S. Aulakh
(74) *Attorney, Agent, or Firm*—Leydig, Voit & Mayer, Ltd.

(57) ABSTRACT

The present invention provides a method for N-deprotecting an opioid compound, a method for N-deprotecting and O-demethylating an opioid compound, a method for O-demethylating an opioid compound, and a method for O-demethylating a nonpeptidic delta agonist compound or an opioid compound having a tertiary amide with no significant reaction at amide groups.

18 Claims, No Drawings

METHODS OF O-DEMETHYLATION AND N-DEPROTECTION

This application is a 371 of PCT/US/97/08628 filed May 21, 1997, and claims priority to Provisional Application No. 60/018,027 filed May 21, 1996 and claims benefit to Provisional Application No. 60/020,215 filed Jun. 21, 1996.

FIELD OF THE INVENTION

The present invention is directed to a method for the N-deprotection of an opioid compound, a method for the N-deprotection and O-demethylation of an opioid compound, a method for the aromatic O-demethylation of an opioid compound, and a method for the selective O-demethylation of a nonpeptidic delta agonist compound or an opicid compound having a hindered amide.

BACKGROUND OF THE INVENTION

An increasing demand for medicinal opiates, coupled with a finite supply of raw materials from opium, has created a need for simple high yielding procedures for opiate transformations.

A 3-phenolic group is essential for the important pharmacological profile of the opium alkaloids and their derivatives (opioid compounds). 3-methyl ethers, such as codeine and thebaine, are the most widely used starting materials for opioid synthesis. Aromatic O-demethylation is a key step in the synthesis of virtually all opioid medical narcotics and their antagonists. Current procedures involve the use of toxic and carcinogenic reagents, such as boron tribromide, propane thiolate, and potassium hydroxide. These reagents have a limited range of applicability and non-toxic alternatives are highly desirable.

Known methods of converting codeine to morphine are not entirely satisfactory. Exposure of codeine or morphine to strong acid or alkaline conditions at higher temperatures has been found to promote substantial decomposition of these opiates. Previously, codeine has been converted to morphine by treatment with acids, such as pyridine hydrochloride, for a brief period at 220° C. or with the toxic boron tribromide. *Journal Med. Chem.*, 20:164–65 (1977). Also, demethylation of a compound similar to codeine has been achieved by use of the diphenyl phosphide ion. The O-demethylation of codeine has also been achieved by treatment with sodium propylmercaptide in dimethylformamide at 125° C. However, none of these previously known methods are desirable due to the need for toxic agents and/or the resulting substantial decomposition of the opiates.

Thebaine has no medicinal use in and of itself, but is a relatively abundant widely used raw material derived from opium. Thebaine is the key intermediate in the synthesis of many opiate derivatives. This is the case for the oripavine derivatives initiated from the Diels-Alder adducts of thebaine. Oripavine is naturally occurring only in extremely minor amounts, but is of interest since it may obviate the final and difficult 3-O-methyl-ether cleavage in the synthesis of Diels-Alder derived narcotics. *Journal of Med. Chem.*, 20:1074–77 (1975). No method for the direct transformation of thebaine to oripavine has been discovered, despite many attempts made over the course of seventy years. Even methods which are undesirable for other opioid conversions due to toxicity or decomposition of the opioid compounds do not work at all for the conversion of thebaine to oripavine. For example, as mentioned above, the O-demethylation of codeine has been achieved by treatment of sodium propylmercaptide in dimethylformamide at 125° C. However, this same procedure applied to thebaine did not yield oripavine. *Journal Med. Chem.*, 20:165–66 (1977).

N-alkylation is also a key step in the synthesis of opioid compounds. Previously known methods that have been developed for N-alkylation have resulted in low yields or were subject to hazards associated with the procedures. For example, in the codeine to norcodeine conversion, N-deprotection of an intermediate carbamate has been accomplished using hydrazine. However, this procedure is less than ideal due to the potential presence of air-sensitive anhydrous hydrazine which is explosive. *J. Org. Chem.*, 40:1850–51 (1975). O-demethylation and N-deprotection may occur simultaneously or one after the other under the proper conditions. Currently, O-demethylation and N-deprotection may occur simultaneously by subjecting the compound to alkaline conditions by heating with potassium hydroxide under vigorous conditions. *J. Amer. Chem. Soc.*, 89:13 (1967). This reaction has been found to be unreliable at times and some compounds are not stable under the vigorous conditions.

L-Selectride®, having the chemical name lithium tri-sec-butylborohydride, has recently been reported as an efficient O-demethylating reagent for simple systems and stable compounds not normally prone to rearrangements or decomposition when subjected to strong acids or bases or hydride reagents. *Tetrahedron Letters*, 35:8727–30 (1994). In contrast, opioid compounds can be very susceptible to rearrangement and decomposition in the presence of strong acids and bases. For example, thebaine is known to be very sensitive to hydride reagents, the epoxide bridge being readily cleaved by hydride reagents. Thus, heretofore, hydride reagents, such as L-Selectride®, have not been used as O-demethylating agents in opioid synthesis.

Never before has it been shown that trialkylborohydride reagents are capable of N-deprotecting an N-protected opioid intermediate or that these hydride reagents can both N-deprotect and O-demethylate such compounds.

Accordingly, it is a principle object of the present invention to provide a method for the N-deprotection of an N-protected opioid intermediate. It is another object of the invention to provide a method for both the N-deprotection and aromatic O-demethylation of the N-protected opioid intermediate without the use of toxic or carcinogenic reagents.

It is also a principal object of the present invention to provide a method for the aromatic O-demethylation of opioids that can be carried out without the use of toxic or carcinogenic reagents. It is a further object of the invention to provide a method for the aromatic O-demethylation of opioids with a hydride reagent. It is yet another object of the invention to provide a method for the aromatic O-demethylation of opioids in which the hydride reagent is a lithium trialkylborohydride.

It is a still further object of the present invention to provide a method for the aromatic O-demethylation of codeine by treatment with L-Selectride® to obtain morphine.

It is another object of the present invention to directly convert thebaine to oripavine by treatment with L-Selectride®.

It is a further object of the present invention to provide a method for the aromatic O-demethylation of a nonpeptidic delta agonist compound or an opioid compound having a tertiary amide group or other amide group resistant to reaction with L-Selectride®.

These and other objects and advantages of the present invention, as well as other inventive features, will be apparent from the description of the invention provided herein.

SUMMARY OF THE INVENTION

The present invention provides a method for the N-deprotection of an opioid compound with a hydride reagent. N-deprotection can be accomplished by admixing an N-protected opioid intermediate of an opioid compound with the hydride reagent and allowing the reagent to react. The present invention further provides a method for the N-deprotection and O-demethylation of an opioid compound which includes admixing an N-protected opioid intermediate of an opioid compound with the hydride reagent.

The present invention further provides a method for the aromatic O-demethylation of opioid compounds with a hydride reagent. Aromatic O-demethylation may be accomplished by admixing an opioid compound with the hydride reagent and allowing the reagent to react, without the use of toxic or carcinogenic agents.

In each of these methods, the hydride reagent is a lithium trialkylborohydride, including lithium tri-sec-butylborohydride (L-Selectride®), lithium trisiamylborohydride (LS-Selectride®), and lithium triethylborohydride (SuperHydride®).

The present invention also provides a direct method for the conversion of thebaine to oripavine by contacting thebaine with lithium tri-sec-butylborohydride(L-Selectride®).

The present invention still further provides a method for the aromatic demethylation of a nonpeptidic delta agonist compound or an opioid compound having a tertiary amide group with minimal or no reaction at the amide group. The delta agonist compound or opioid compound is admixed with lithium tri-sec-butylborohydride (L-Selectride®) or lithium trisiamyiborohydride (LS-Selectride®).

DETAILED DESCRIPTION OF THE PREFERRED EMBODIMENTS

In accordance with the invention, it has been found that opioid compounds and their intermediates are not decomposed by certain hydride reagents. Instead, hydride reagents are capable of N-deprotecting the N-protected opioid intermediates of the opioid compounds. Further, these N-protected opioid intermediates may also be O-demethylated by the hydride reagents. In this way, important N-norphenolic intermediates can be formed.

The opioid compounds which are suitable for use in the method of this aspect of the present invention preferably have protective groups bonded to the nitrogen of the opioid compound. These protective groups generally are present in the opioid compounds in place of the methyl group commonly found in natural opiates.

The protective group bonded to the nitrogen of the opioid compounds may be any protective group known in the art. Preferably, the protective group and the nitrogen of the opioid compound form a cyanamide or a carbamate.

Examples of other suitable compounds that can be used to form the protective group, such as 2,2,2-trichloroethyl chloroformate and benzyl or ethyl chloroformate, can be found in *J. Org. Chem.*, 40:1850–51 (1975) which is incorporated herein by reference.

In accordance with the present invention, N-methyl-containing opioid compounds are preferably converted to intermediates, or N-protected opicid intermediates, which possess an N-protected group that can be cleaved by a hydride reagent. The opioid compounds may be converted to N-protected opioid intermediates by any method known in the art.

The N-protected opioid intermediate can then be reacted with the desired hydride reagent. The method of the present invention permits the introduction of other substituents, converting the N-methyl agonist opioid compounds to opiate antagonist compounds, pharmacologically important compounds.

Generally, the hydride reagent causes O-demethylation in addition to the N-deprotection of the opioid intermediates. In keeping with the method of the present invention, the hydride reagent and N-protected opioid intermediate are admixed in a suitable vessel and allowed to react. The hydride reagent demethylates the aromatic methoxy group and N-deprotects the N-protected group producing the desired N-norphenolic compounds.

The aromatic O-demethylation and N-deprotection reactions may be carried out over a wide temperature range, generally at any temperature which permits the opioid intermediate and the hydride reagent to react. Preferably the reaction is carried out at about 20° C. to about 70° C. While the reaction may be carried out at about room temperature, i.e., about 20° C. to about 25° C., it is preferred that the reaction be carried out at an elevated temperature, i.e., from about 25° C. to about 70° C., to increase the rate of the reaction. It is thus preferred that the reagents be refluxed to accomplish O-demethylation and N-deprotection. It is preferred that the reagents be refluxed in THF (tetrahydrofuran), as L-Selectride® is supplied in a solution of THF. Other solvents may be added for solubility reasons, preferably solvents that do not react with L-Selectride® including, but not limited to, aliphatic ethers (tetrahydropyran, diethyl ether, t-butyl methyl ether), hydrocarbon solvents (hexanes, benzene, toluene), and chlorinated aromatic solvents (chlorobenzene).

The hydride reagents suitable for use in the method of the present invention are those hydrides which do not decompose or cause rearrangement of the N-protected opioid intermediate. Thus, suitable hydride reagents are desirably site specific to the aromatic O-methoxy group and the N-protected group. Satisfactory hydride reagents are lithium trialkylborohydrides which preferably include trisiamylborohydride (LS-Selectride®), lithium triethylborohydride (SuperHydride®), and lithium tri-sec-butylborohydride (L-Selectride®). The most preferred hydride reagent is lithium tri-sec-butylborohydride.

The method of the present invention can be used for the N-deprotection and O-demethylation of opioid compounds generally. By way of illustration and not in limitation, the method of the present invention can be used to N-deprotect and O-demethylate the N-protected opioid intermediates of codeine, thevinols, indoles, oxycodone and derivatives thereof.

While not being bound to any particular theory, it is believed that the hydride reagents, particularly tri-sec-butylborohydride (L-Selectride®), act by allowing demethylation of the N-protected opioid intermediates, while the steric bulk prevents close approach to the C-5 and hence cleavage of the ether bridge. Thus, it is believed that the steric bulk of L-Selectride® minimizes reaction with the labile ether bridge.

Treatment of the N-protected opioid intermediates, e.g., dihydrocodeinone-6-ketal, thevinols and the like, with a hydride reagent results in aromatic O-demethylation and N-deprotection providing important N-norphenolic compounds which are key intermediates in the synthesis of important opioid antagonists such as naltrexone, naloxone and diprenorphine, and the important opioid analgesic buprenorphine. Examples of such O-demethylation and N-deprotection can be found in schemes I and II below.

Scheme I

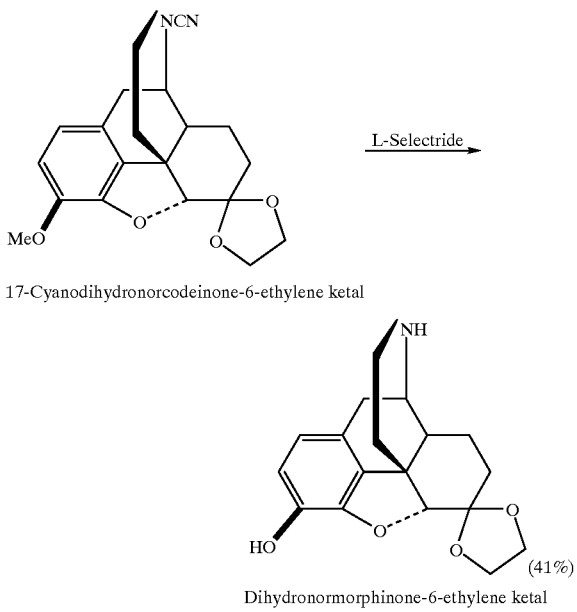

17-Cyanodihydronorcodeinone-6-ethylene ketal

Dihydronormorphinone-6-ethylene ketal (41%)

Scheme II

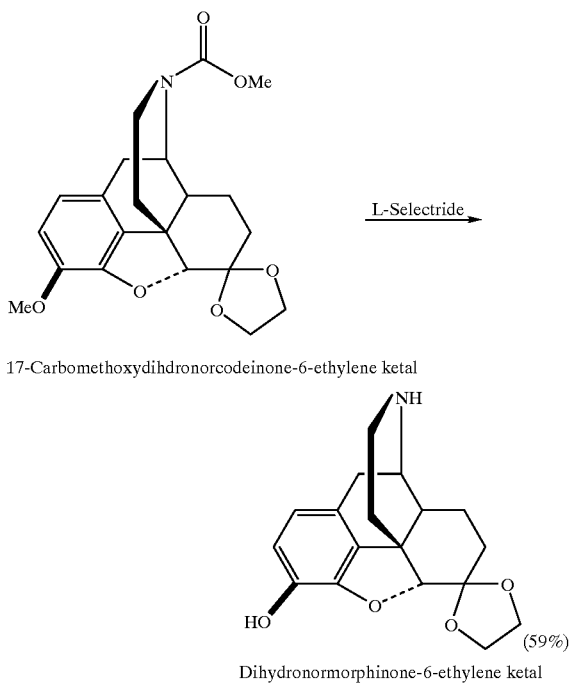

17-Carbomethoxydihdronorcodeinone-6-ethylene ketal

Dihydronormorphinone-6-ethylene ketal (59%)

The same O-demethylation and N-deprotection reactions occur with the 14-hydroxy derivatives, e.g., indoles and oxycodone, to give the desired N-norphenolic products, but the reaction is complicated by side products.

Although O-demethylation and N-deprotection may occur simultaneously or in any sequence, it is believed that in many cases the N-deprotection occurs prior to the O-demethylation because the N-deprotection reaction is believed to occur more quickly than the O-demethylation reaction.

In some instances, O-demethylation may not occur, resulting in opioid compounds that have only been N-deprotected. Further, because the N-deprotection reaction occurs far more rapidly than O-demethylation, perhaps even spontaneously at room temperature, the present invention allows for selective N-deprotection of opioid compounds. Therefor, it is preferable that the reaction is not refluxed, but kept cold to minimize O-demethylation. If the reaction between the N-deprotected opioid intermediate and the hydride reagent is halted after N-deprotection occurs and prior to O-demethylation, opioid compounds may be obtained which have not been O-demethylated, but which have been selectively N-deprotected. The reaction with the hydride reagent may be halted by any means known in the art. For example, opioid compounds which may be selectively N-deprotected include, but are not limited to, N-protected opioid intermediates of thevinols, indoles, codeine, oxycodone and derivatives thereof. An example of the N-deprotection of 17-carbomethoxynorcodeinone to norcodeine is set forth in Scheme III below.

Scheme III

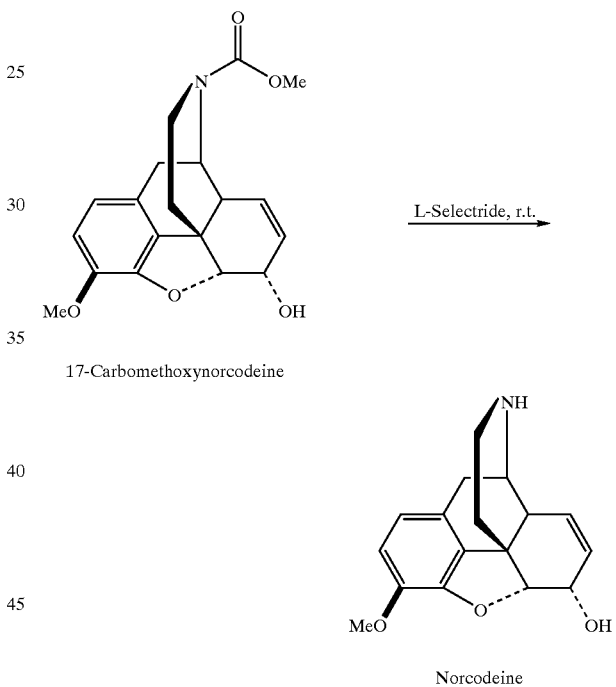

17-Carbomethoxynorcodeine

Norcodeine

In accordance with another embodiment of the present invention, the hydride reagents are capable of O-demethylating the opioid compounds. In keeping with this aspect of the present invention, the hydride reagent and opioid compound are admixed in a suitable vessel and allowed to react. The hydride reagent demethylates the aromatic methoxy group leaving the desired phenol derivative.

The aromatic O-demethylation reaction may likewise be carried out over a wide temperature range, i.e, from about 20° C. to about 70° C. While the reaction may be carried out at about room temperature, i.e., about 20° C. to about 25° C., it is preferred that the reaction be carried out at elevated temperatures to increase the rate of the reaction. It is thus preferred that the mixture of reagents be refluxed to accomplish O-demethylation.

The hydride reagents suitable for use in the method of aromatic O-demethylation are likewise those hydride reagents which do not decompose or cause rearrangement of the opioid compound and are desirably site specific to the aromatic methoxy group. Satisfactory hydride reagents include the lithium trialkylborohydrides, such as trisiamylborohydride (LS-Selectride®), lithium triethylborohydride (SuperHydride®), and lithium tri-sec-butylborohydride (L-Selectride®). The preferred hydride reagent is lithium tri-sec-butylborohydride.

The method of the present invention can be used for the aromatic o-demethylation of opioid compounds generally. By way of illustration and not in limitation, the method of the present invention may be used to O-demethylate thebaine, thevinols, indoles, codeine, oxycodone and the like.

The discovery that thebaine can be converted to oripavine with a hydride reagent is an unexpected discovery of the present invention. Despite many efforts over more than sixty years, there has been no direct method for the O-demethylation of thebaine to oripavine, due in large part to the sensitivity of the allylic aromatic ether to acids, bases and nucleophiles. Since oripavine occurs in opium in extremely minor amounts, while thebaine is relatively abundant by comparison, direct O-demethylation of thebaine in accordance with the invention offers a practical synthesis of oripavine. The direct synthesis of oripavine resulting from the admixture of thebaine and L-Selectride® is set forth in Scheme IV:

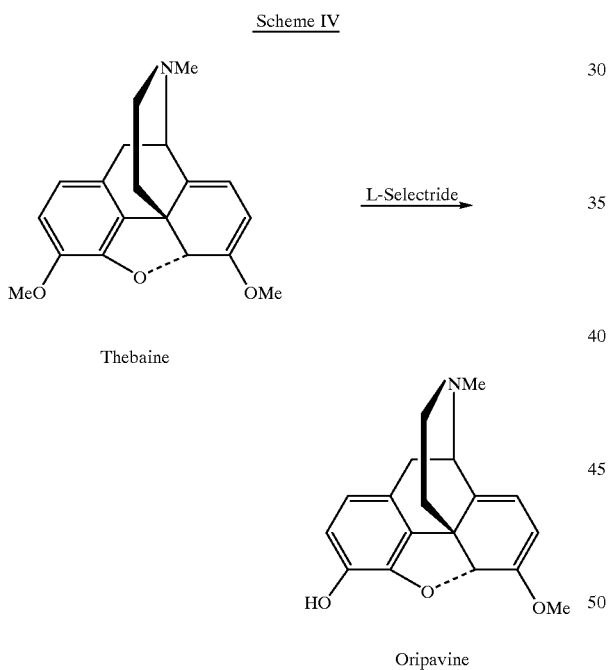

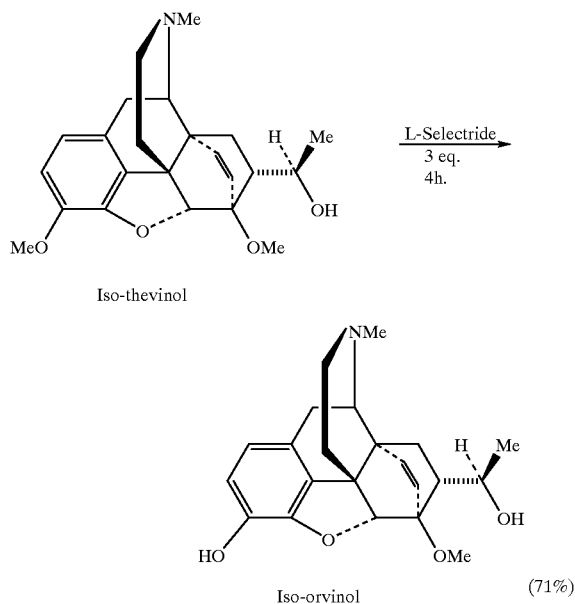

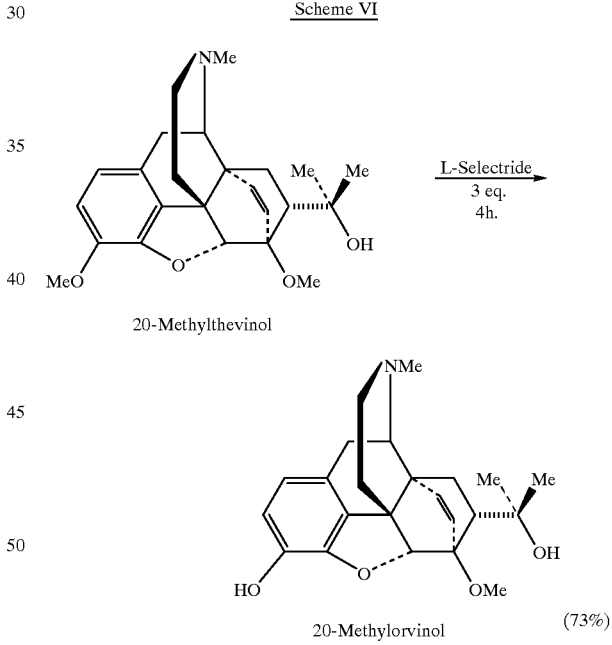

The ready availability of oripavine obtained by treatment of thebaine with L-Selectride® allows the synthesis of compounds currently prepared from thebaine without the need for further O-demethylation. Syntheses of important opioids, such as diprenorphine and nalzrexone, from oripavine can be easily achieved by application of the present invention.

Some opioid compounds, such as thevinols, are sensitive to acid which often makes O-demethylation difficult. However, treatment of thevinols with L-Selectride® results in clean conversions to the corresponding phenols (orvinois). Representative reactions are described in Schemes V and VI.

Indoles are important opioid compounds due to their δ opioid receptor selectivity. This receptor has been associated with many biological Drocesses, thereby providing for δ selective medication. Successful aromatic O-demethylation in the indole series offers an important alternative synthesis for the phenols derived from indoles. Treatment with L-Selectride® provides demethylation of the indoles to the corresponding phenols as shown in Scheme VII.

Scheme VII

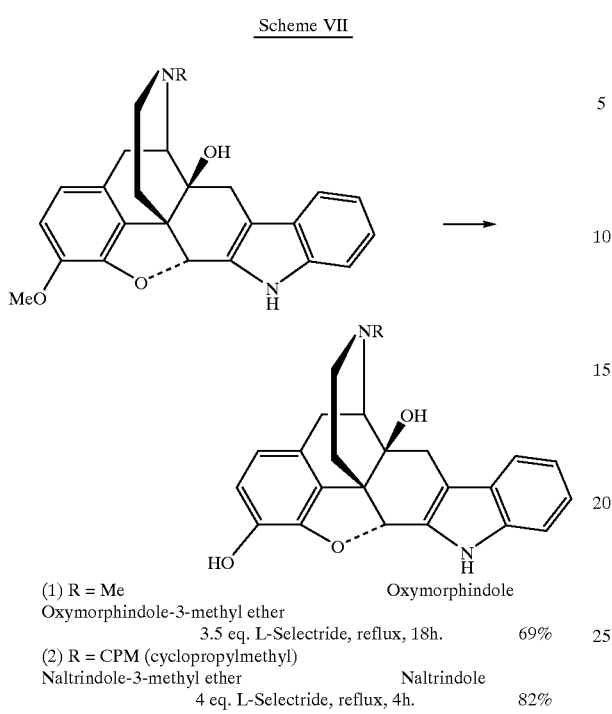

(1) R = Me      Oxymorphindole
Oxymorphindole-3-methyl ether
    3.5 eq. L-Selectride, reflux, 18h.     69%
(2) R = CPM (cyclopropylmethyl)
Naltrindole-3-methyl ether      Naltrindole
    4 eq. L-Selectride, reflux, 4h.     82%

The O-demethylation of codeine to morphine can be accomplished satisfactorily without toxic or carcinogenic reagents using L-Selectride® according to Scheme VIII.

The conversion of oxycodone to oxymorphone is an important commercial transformation which is performed with boron tribromide. This transformation can also be made with L-Selectride as shown in Scheme IX, a significant improvement in both convenience and toxicity considerations.

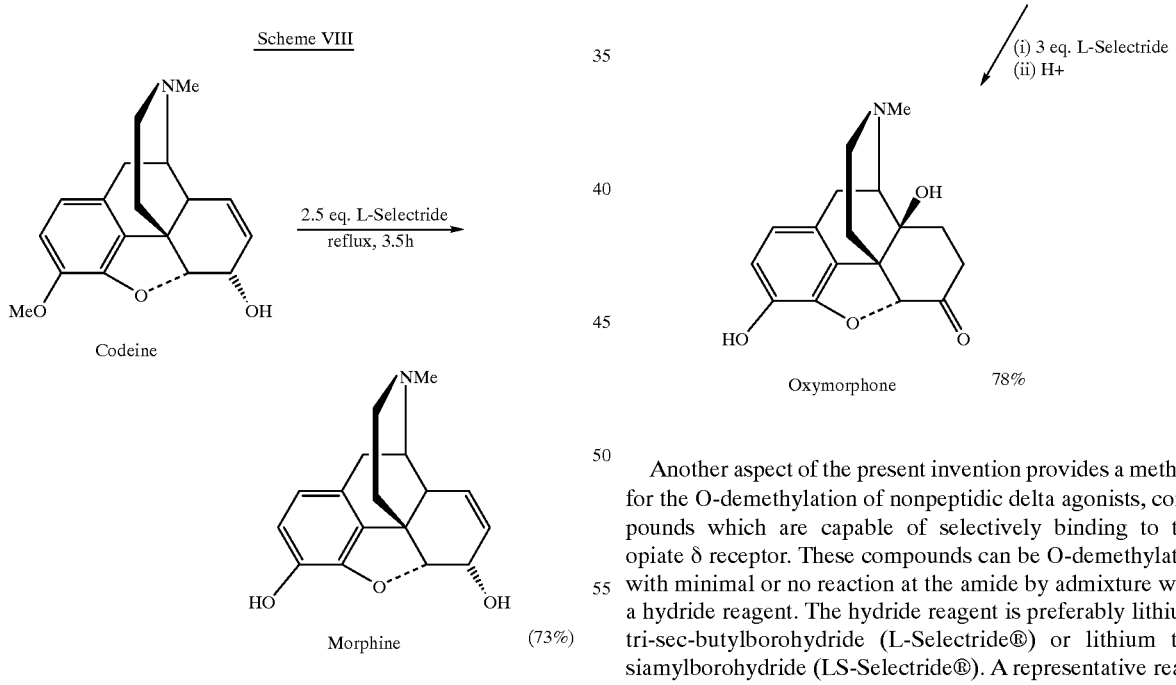

Another aspect of the present invention provides a method for the O-demethylation of nonpeptidic delta agonists, compounds which are capable of selectively binding to the opiate δ receptor. These compounds can be O-demethylated with minimal or no reaction at the amide by admixture with a hydride reagent. The hydride reagent is preferably lithium tri-sec-butylborohydride (L-Selectride®) or lithium tri-siamylborohydride (LS-Selectride®). A representative reaction is shown in Scheme X.

Scheme X

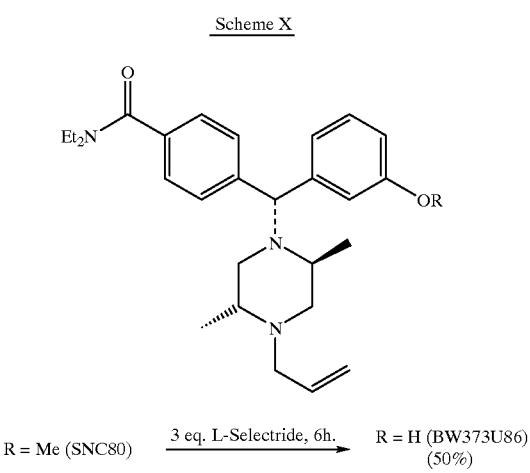

R = Me (SNC80) →(3 eq. L-Selectride, 6h.) R = H (BW373U86) (50%)

The use of lithium triethylborohydride (SuperHydride®) in this aspect of the invention is not desirable because it is known to cleave amide groups. However, it is believed that the reason lithium tri-sec-butylborohydride and lithium tri-siamylborohydride O-demethylate without cleavage of the amide is because of the large size of the lithium tri-sec-butylborohydride and lithium trisiamylborohydride molecules.

BW373U86, shown in Scheme X, is a novel non-peptide δ opioid receptor racemic agonist which is useful in the discovery of new probes for the δ receptor system. The method of the present invention is suitable for use with any nonpeptide delta agonist compound having a related structure and a tertiary amide group or an amide group that is resistant to reaction with L-Selectride®. The hindered amide group may be any amide group that is resistant to reaction with L-Selectride® including, but not limited to, amides that are N-N-disubstituted with alkyl, arylalkyl or aryl groups. Preferable compounds include (+)-4-[(αR)-α((2S,5R)-4-allyl-2,5-dimethyl-1-piperazinyl)-3methoxybenzyl]-N,N-diethylbenzamide (SNC80) and other compounds having a structure similar to SNC80 and a hindered tertiary amide group or amide group that is resistant to reaction with L-Selectride®. This method is also applicable to opioid compounds having a tertiary amide group and compounds with opioid-like structures having a tertiary amide groups resistant to reaction with L-Selectride(D. Again, the hindered amide group may be any amide group that is resistant to reaction with L-Selectride® including, but not limited to, amides that are N,-N-disubstituted with alkyl, arylalkyl, or aryl groups.

Again, the aromatic O-demethylation may be carried out over a wide temperature range. The reaction may be carried out at room temperature, i.e., about 20 C. to about 25° C., but it is preferred that the reaction be carried out at an elevated temperature, i.e., from about room temperature up to about 70° C. It is preferred that the reagents be refluxed in THF to accomplish the O-demethylation. Other solvents may be added for solubility reasons, preferably solvents that do not react with L-Selectride® including, but not limited to, aliphatic ethers (tetrahydropyran, diethyl ether, t-butyl methyl ether), hydrocarbon solvents (hexanes, benzene, toluene), and chlorinated aromatic solvents (chlorobenzene).

General Synthetic Methods

The lithium trialkylborohydrides, as is known, are extremely reactive with oxygen and water. See, Aldrich *Catalog Handbook of Fine Chemicals*, p. 908 (1996–97). Accordingly, each of the reactions described above are preferably carried out in an inert atmosphere, such as argon, nitrogen, or the like, as one skilled in the art would readily appreciate. B. S. Furniss et al., *Vogle's Textbook of Practical Organic Chemistry*, Longman Scientific and Technical, John Wiley & Sons, Inc., N.Y., pp. 120–131 (5th ed.1989).

After the reaction is complete according to any of the methods described herein, the desired end product is isolated and purified by techniques well known to those skilled in the art. Accordingly, after quenching of the excess hydride reagent with water, the mixture is basified to pH 14 with preferably, potassium hydroxide or sodium hydroxide. The reaction solvent (e.g., tetrahydrofuran) is removed from the reaction vessel, preferably under reduced pressure. The reaction mixture is then washed with a known organic solvent. Suitable solvents include ethers, halogenated solvents such as dichloromethane, chloroform, and the like, and mixtures of halogenated solvents and alcohols, including methanol, ethanol, propanols, and the like, as described, for example, in *Journal Med. Chem.*, 18:1074–77 (1975), which is incorporated by reference herein.

The washed product mixture is then acidified to a pH range of from about 1 to about 3. The acid may be a dilute aqueous solution of organic acid such as citric acid, acetic acid and formic acid, or a dilute aqueous solution of inorganic acid, such as hydrochloric acid, phosphoric acid, sulfuric acid and hydrobromic acid.

The acidified reaction product is then rebasified to a pH in the range of from about 7 to about 10, preferably about 9. Suitable basification agents include concentrated aqueous ammonia solution, an aqueous solution of sodium bicarbonate, and the like.

If the end product is not soluble in the aqueous base layer solution, then the reaction is simply quenched with water, followed by acidification to pH 1, then basification to pH 7–10.

The phenolic product is then extracted from the aqueous layer using ethers, halogenated solvents such as dichloromethane, chloroform, and the like, mixtures of halogenated solvents and alcohols, including methanol, ethanol, propanols, and the like, ethyl acetate, and aromatic solvents such as benzene, toluene and the like.

The purified end product is obtained by crystallization or chromatography by techniques well known in the art, such as described in B. S. Furniss et al., *Vogle's Textbook of Practical Organic Chemistry*, Longman Scientific and Technical, John Wiley & Sons, Inc., N.Y., pp. 131–235 ($_5$th ed.1989) which is incorporated by reference herein.

It will be appreciated by those skilled in the art that the aromatic O-demethylation, N-deprotection, combined O-demethylation and N-deprotection, and selective O-demethylation of nonpeptidic delta agonists and opioid compounds having a hindered tertiary amide or otherwise unreactive amide processed as described herein, can be applied to derivatives of the opioid compounds as well. Thus, opioid compounds that have been derivatized with organic moieties such as alkyls, alkenyls, alkynyls, aryls, arylalkyls, ethers, aromatic halogens, and the like that are inert to reaction with hydride reagents, can also be O-demethylated and/or N-deprotected in accordance with the methods described above with the lithium trialkylborohydrides, especially those described above.

Further, the reducing properties of the lithium trialkylborohydrides, such as L-Selectride®, can be exploited by reducing opioid compounds that have been derivatized with organic moieties, such as carbonyl or the like, with simultaneous O-demethylation. For example, in the conversion of dihydrocodeinone to dihydromorphine, dihydrocodeinone is both reduced and O-demethylated to obtain dihydromorphine.

The present inventive methods are further described in the context of the following examples. These examples serve to illustrate further the present invention and are not intended to limit the scope of the invention.

EXAMPLE 1

This example illustrates the synthesis of dihydronormorphinone-6-ethylene ketal by N-deprotection and O-demethylation of a carbamate (an N-protected opioid intermediate) with tri-sec-butylborohydride (L-Selectride®).

Under an inert atmosphere (argon), a mixture of the carbamate (17-carbomethoxydihydronorcodeinone-6-ethylene ketal) (520 mg, 1.3 mmol) and L-Selectride (1 M in THF, 12.5 ml) was heated at reflux for 4.5 hours. After cooling to room temperature, the reaction was quenched with water (10 ml) and NaOH (1 M, 5 ml). The THF was removed under reduced pressure and the mixture was washed with dichloromethane, acidified (pH 1) with hydrochloric acid (10%) and rebasified (pH 9) with ammonia solution. The aqueous solution was saturated with salt and extracted with chloroform/methanol (3:1). After removal of the solvents, the product was isolated as the hydrochloride salt from methanol (280 mg, 59%).

Mp.>300° C. (dec.); $\delta_H$ (300 MHz, $D_2O$) (HCl salt) 2.98 (1H, d j 18.5 Hz, 10β-H), 4.70 (1H, δ5-H), 6.76 (1H, d j 8.2 Hz, 1-H), 6.82 (1H, d j 8.2 Hz, 2-H); m/z (CS LSMIS) 316 (M+1, 100%); Calc. For $C_{18}H_{22}NO_4Cl$ C 61.45; H, 6.30; N 3.98, found C 61.28; H, 6.30; N, 3.93.

EXAMPLE II

This example illustrates the synthesis of norcodeine from 17-Carbomethoxynorcodeine by N-deprotection (without O-demethylation) with lithium trt-sec-butylborohydride (L-Selectride®) (see Sheme III).

Lithium tri-sec-butylbcrohydride (L-Selectride®) (1M in THF, 5 ml) was added to a cooled (0–5° C.) solution of 17-carbomethoxynorcodeine (300 mg, 0.87 mmol) in dry THF (2 ml) under an atmosphere of argon. The reaction mixture was allowed to warm to room temperature and then stirred for 24 hours. After quenching the reaction with water (10 ml), the THF was removed under reduced pressure and the remaining aqueous mixture acidified to pH 1–2 with citric acid (15%) and washed with chloroform (2×30 ml). After basification with ammonia solution, the mixture was extracted into chloroform (3×50 ml) which was then washed with brine and dried ($Na_2SO_4$). Purification as the hydrochloride salt from water gave norcodeine hydrochloride trihydrate (275 mg, 83%).

Mp>300° C.; $\delta_H$ (300 MHz, $CDCl_3$) 3.61–3.67 (1H, s br) 3.81 (3H, s, 3-$OCH_3$), 4.16–4.21 (1H, m, 6-H), 4.84 (1H, d j 6.2 Hz, 5-H), 522–5.29 (1H, m, 7-H), 5.68–5.76 (1H, m, 8-H), 6.58 (1H, d j 8.2 Hz, 1-H), 6.64 (1H, d j 8.2 Hz, 2-H; m/z (EI) 285 (M+, 100%).

EXAMPLE III

This example illustrates the synthesis of oripavine from thebaine by admixing thebaine with lithium tri-sec-butylborohydride (L-Seiectride®)(See Scheme IV).

Under an inert atmosphere (argon), a mixture of thebaine (3.64 g, 11.7 mmol) and lithium tri-sec-butylborohydride (L-Selectride®) (1M in THF, 60 ml) was stirred at room temperature for 14 days. The reaction was quenched with water (50 ml) followed by aqueous NaOH solution (15%, 30 ml) and the THF removed under reduced pressure. The resulting mixture was washed with dichloromethane (2×50 ml) and acidified (pH 1) with hydrochloric acid (10%). After basification with ammonia solution (pH 9), the mixture was extracted into chloroform (3×60ml) and the organic phase washed with brine (100 ml) and dried ($Na_2SO_4$). Removal of the solvent under reduced pressure gave the crude oripavine product. Crystallization as the oxalate salt from methanol gave oripavine oxalate (1.69 g, 35%).

Mp. 198–200° C. (dec.); $\delta_H$ (300 MHZ,$CDCl_3$) 2.45 (3H, s, $NCH_3$), 3.31 (1H, d j 18.5 Hz, 10β-H), 3.59 (3H, s, 6-$OCH_3$), 5.04 (1H, d j 6.2 Hz, 8-H), 5.28 (1H, s, 5-H), 5.55 (1H, d j 6.2 Hz, 7-H), 6.54 (1H, d j 8.2 Hz, 1-H) 6.62 (1H, d j 8.2 Hz, 2-H); m/z (CI) 298 (M+1, 100%); Calc. For $C_{20}H_{21}NO_7 \cdot 1.5 H_2O$ C, 57.96; H, 5.84; N, 3.38, found C, 58.22; H, 5.82; N, 3.41.

The original dichloromethane extracts obtained above were washed with water (2×100 ml), followed by brief treatment with basic peroxide. The organic laver was separated, washed with brine (100 ml) and dried ($Na_2SO_4$) Removal of the solvent under reduced pressure gave a brown foam. Crystallization as the natural tartrate salt from methanol gave thebaine tartrate (270 mg, 5%).

EXAMPLE IV

This example illustrates a second method for the synthesis of oripavine from thebaine by admixing thebaine with tri-sec-butylborohydride(L-Selectride®)(See Scheme IV).

The method of Example 1 above was followed, but 2 equivalents of tri-sec-butylborohydride (L-Selectride®) were used and the mixture was refluxed for 30 minutes to give oripavine oxalate hydrate (23%) and thebaine tartrate (31%).

EXAMPLE V

This example illustrates the synthesis of oxymorphone from oxycodone by admixing oxycodone with tri-sec-butylborohydride (L-Selectride®) (See Scheme IX).

A solution of oxycodone HCl (29.5 g, 6.9 mmol), ethylene glycol (5 ml) and catalytic toluene sulfonic acid in dry toluene (200 ml) was heated at reflux for 1 hour with azeotropic removal of water. After cooling, the solution was basified with ammonia solution and partitioned between water and chloroform and the aqueous phase was further extracted with chloroform. The organic extracts were washed with brine and dried ($Na_2SO_4$). Removal of the solvent gave the crude ketal (2.46 g).

Under an inert atmosphere (argon), a mixture of the ketal and tri-sec-butylborohydride (L-Selectride®) (0.5M in THF, 40 ml) was heated at reflux for 23 hours. The reaction was quenched with water (20 ml) followed by aqueous NaOH solution (15%, 15 ml) and the THF removed under reduced pressure. The resulting mixture was washed with dichloromethane (2×20 ml) and acidified (pH 1) with hydrochloric acid (10%). After basification with ammonia solution (pH 9), the mixture was extracted into chloroform (3×40 ml) and the organic phase washed with brine and dried ($Na_2SO_4$). Removal of the solvent under reduced pressure gave a crude foam. The foam was redissolved in methanol (40 ml), water (20 ml) and hydrochloric acid (20%, 20 ml) and the solution refluxed for 1 hour. After cooling, the reaction was diluted with water (50 ml), basified with ammonia (pH9), saturated with salt, and extracted into chloroform (3×70 ml). After removal of the solvent under reduced pressure, the product was crystallized as the oxalate salt from ethanol. (2.11 g, 78%).

Mp.247–248° C. (dec.) $\delta_H$ (300 MHz, CDCl$_3$) 2.41 (3H, s, NCH$_3$), 3.15 (1H, d j 18.5 Hz, 10β-H), 4.68 (1H, s, 5-H) 6.60 (1H, d j 8.2 Hz, 1-H), 6.72 (1H, d j 8.2 Hz, 2-H); m/z (CI) 302 (M+1, 100%); Calc. for C$_{19}$H$_{21}$NO$_8$ C58.31; H 5.41; N 3.58, found C, 57.94; H, 5.44; N, 3.56.

EXAMPLE VI

This example illustrates the synthesis of naltrindole.

Under an inert atmosphere, (argon), a mixture of the methyl ether (240 mg, 0.56 mmol)(See Scheme VII) and tri-sec-butylborohydride (L-Selectride®) (1M in THF, 2.5 ml) was heated at reflux for 4 h. After cooling the reaction was quenched with water (10 ml) and NaOH (15%, 10 ml). After removal of the THF, the aqueous solution was extracted with dichloromethane (2×20 ml). The organic extracts were then washed with brine (30 ml), dried (Na$_2$SO4) and the solvent removed under reduced pressure to give a foam. Formation of the hydrochloride salt in methanol, followed by replacement of the solvent with isopropanol, gave the salt (225 mg, 82%).

Mp. <275° C. (dec.); $\delta_H$ (300 MHz, CDCl$_3$) 0.12–2.00 (2H, m), 0.53–0.62 (2H, m), 0.81–0.95 (1H, m), 3.12 (1H, d j 18.5 HZ, 10-βH), 5.69 (1H, s, 5-H), 6.50 (1H, d j 8.2 Hz, 1-H), 6.58 (1H, d j 8.2 Hz, 2-H), 6.96–7.42 (4H, m, Ar—H), 8.22 (1H, br s, N—H); m/z (Cl) 415 (M+1, 64%); Calc. For C$_{26}$H$_{27}$N$_2$O$_3$Cl.CH$_3$OH C, 67.14; H, 6.47; N, 5.80, found C, 66.93; H, 6.28; N, 5.71.

EXAMPLE VII

This example illustrates the synthesis of the delta agonist (+)-BW373U86 by O-demethylation without significant reaction at the amide group with tri-sec-butylborohydride (L-Selectride®) (See Scheme X).

Under an inert atmosphere (argon), a mixture of SNC80, as shown in Scheme III (740 mg, 1.65 mmol), and lithium tri-sec-butylborohydride (L-Selectride®) (1M in THF, 5 ml) was heated at reflux for 6 hours, cooled to room temperature and then quenched with water (20 ml). After removal of the THF under reduced pressure, the mixture was acidified (pHI) with hydrochloric acid (10%), rebasified (pH9) with ammonia solution and extracted into dichlormethane (3×40 ml). The organic extracts were then washed with brine (2×50 ml), dried (Na$_2$SO$_4$) and the solvent removed under reduced pressure to give the crude product. Column chromatography (Silica, CH$_2$Cl$_2$:EtOAc 1:1, 0.5% NH$_3$) gave the desired product (360 mg, 50%).

Ditoluoyl-L-tartrate salt; mp 151–153° C.; $\delta_H$ (300 MHz, CDCl$_3$) 0.95 (3H, d j 6.0 Hz, CCH$_3$) 1.15–1.28 (9H, m), 1.91 (1H, br t), 2.15 (1H, br t), 5.11–5.24 (3H, m), 5.78–5.93 (1H, m), 6.57 (1H, S), 6.61–6.67 (2H, m), 7.07–7.13 (1H, m), 7.28 (2H, d j 8. 2 Hz), 7.42 (2H, d j 8.2 HZ); m/z (Cl) 436 (M+1, 76%); Calc. For C$_{26}$H$_{27}$,N$_2$O$_3$Cl.CH$_3$OH C 67.14; H 6.47; N 5.80, found C 66.93; H 6.28; N 5.71. Calc. For C$_{47}$H$_{55}$N$_3$O$_{10}$ 1.5H$_2$O C 66.49; H 6.89; N, 4.95, found C 66.58; H, 6.75; N, 4.90.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for the aromatic O-demethylation of an opioid compound comprising admixing said opioid compound and a hydride reagent selected from the group consisting of lithium tri-sec-butylborohydride, lithium trisiamylborohydride and lithium triethylborohydride to produce an O-demethylated opioid compound, wherein the yield of the O-demethylated opioid compound is at least 23%.

2. The method of claim 1, wherein said hydride reagent is lithium tri-sec-butylborohydride.

3. The method of claim 1, wherein said opioid compound is selected from the group consisting of thebaine, codeine, thevinols, indoles, and oxycodone.

4. The method of claim 3, wherein thevinols are O-demethylated to orvinols.

5. The method of claim 3, wherein codeine is O-demethylated to morphine.

6. The method of claim 3, wherein oxycodone is O-demethylated to oxymorphone.

7. The method of claim 3, wherein thebaine is O-demethylated to oripavine.

8. A direct method for the preparation of oripavine from thebaine comprising admixing thebaine with lithium tri-sec-butylborohydride.

9. A method for the aromatic O-demethylation of an opioid compound comprising admixing said opioid compound with a hydride reagent selected from the group consisting of lithium tri-sec-butylborohydride, lithium trisiamylborohydride and lithium triethylborohydride, and refluxing the mixture, to produce an O-demethylation opioid compound, wherein the yield of the O-demethylated opioid compound is at least 23%.

10. The method of claim 9, wherein said hydride reagent is lithium tri-sec-butyiborohydride.

11. The method of claim 9, wherein said opioid compound is selected from the group consisting of thebaine, codeine, thevinols, indoles, and oxycodone.

12. The method of claim 11, wherein thevinols are O-demethylated to orvinols.

13. The method of claim 11, wherein codeine is O-demethylated to morphine.

14. The method of claim 11, wherein oxycodone is O-demethylated to oxymorphone.

15. The method of claim 11, wherein thebaine is O-demethylated to oripavine.

16. A method for the aromatic O-demethylation of an opioid compound having at least one amide group with minimal or no reaction at the amide group comprising admixing said opioid compound and a hydride reagent selected from the group consisting of lithium tri-sec-butylborohydride and lithium trisiamylborohydride.

17. A method for the aromatic O-demethylation of an opioid compound comprising admixing at a temperature of about 20° C. to about 70° C. said opioid compound and a hydride reagent selected from the group consisting of lithium tri-sec-butylborohydride, lithium trisiamylborohydride and lithium triethylborohydride to produce an O-demethylated opioid compound.

18. A method for the aromatic O-demethylation of an opioid compound comprising, at a temperature of about 20° C. to about 70° C., admixing said opioid compound with a hydride reagent selected from the group consisting of lithium tri-sec-butylborohydride, lithium trisiamylborohydride and lithium triethylborohydride, and refluxing the mixture, to produce an O-demethylated opioid compound.

* * * * *